United States Patent [19]

Brinkley et al.

[11] Patent Number: 5,326,692
[45] Date of Patent: Jul. 5, 1994

[54] FLUORESCENT MICROPARTICLES WITH CONTROLLABLE ENHANCED STOKES SHIFT

[75] Inventors: John M. Brinkley, Elmira; Richard P. Haugland; Victoria L. Singer, both of Eugene, all of Oreg.

[73] Assignee: Molecular Probes, Inc., Eugene, Oreg.

[21] Appl. No.: 882,299

[22] Filed: May 13, 1992

[51] Int. Cl.$^5$ ............... C12Q 1/68; G01N 33/545; C09K 11/02
[52] U.S. Cl. .................. 435/6; 435/7.92; 436/518; 436/528; 436/529; 436/531; 436/546; 436/800; 428/402; 252/301.34; 252/301.35
[58] Field of Search ............ 435/6, 7.1, 7.5, 7.92; 436/518, 528, 529, 520, 531, 546, 800; 427/213.34, 157; 428/40 R, 402.24, 407; 252/301.34, 301.35

[56] References Cited

U.S. PATENT DOCUMENTS

| | | | |
|---|---|---|---|
| 2,994,697 | 8/1961 | Eckert et al. | 260/282 |
| 3,096,333 | 7/1963 | Wilson et al. | 260/281 |
| 4,326,008 | 4/1982 | Rembaum | 428/503 |
| 4,520,110 | 5/1985 | Stryer et al. | 436/501 |
| 4,542,104 | 9/1985 | Stryer et al. | 428/341 |
| 4,666,862 | 5/1987 | Chan | 436/501 |
| 4,774,339 | 9/1988 | Haugland et al. | 548/405 |
| 4,808,524 | 2/1989 | Snyder et al. | 435/36 |
| 4,916,711 | 4/1990 | Boyer et al. | 372/53 |
| 4,997,597 | 3/1991 | Clough et al. | 252/646 |

OTHER PUBLICATIONS

Flow Cytometry and Sorting, 2nd ed., ch. 20, Wiley-Liss, Inc., New York (1990).
Hook et al. J Leukocyte Biol 45, 277 (1989).
Confocal Microscopy Handbook, p. 154 (rev. ed. 1990).
Molday, et al., J Cell Biol 64, 75 (1975).
Oi, et al., J Cell Biol 93, 981 (1982).
Gorelenko, et al., *Photonics of Bichromophores Based on Laser Dyes in Solutions and Polymers,* Experimentelle Technik Der Physik 37, 343 (1989).
Stryer & Haugland, *Energy Transfer: A Spectroscopic Ruler,* Proc Natl. Acad SCI USA 58, 719 (1967).
Haugland, Yguerabide, & Stryer, *Dependence of the Kinetics of Singlet-Singlet Energy Tansfer on Spectral Overlap,* Proc Natl Acad SCI USA 63, 23 (1969).
Jullien & Garel, Biochemistry 22, 3829 (1983).
Wooley, et al., Biophys Chem 26, 367 (1987).
Ohmine, et al., Macromolecules 10, 862 (1977).
Drake, et al., Science 251, 1574 (1991).
Saito, et al., Appl Phys Lett 56, 811 (1990).
Kuh, *Production of Simple Organized Systems of Molecules,* Pure Appl Chem 11, 345 (1966), abstracted in Chem Abstracts 66, 671 (1967).
Yamazaki, et al., J Phys Chem 94, 516 (1990).
Mataga, et al., J Phys Chem 73, 370 (1969).
Bennett, J Chem Physics 41, 3037 (1964).
Bangs (Uniform Latex Particles (1984, Seragen, Inc.).
Tsein Chem Soc Rev 2, 249 (1973).
Nathan et al. J Exp Med 154, 1539 (1981).
Vener, et al., Anal Biochem 198, 308 (1991).
Wolf, et al., Nucleic Acids Res 15, 2911 (1987).
Kremsky, et al., Nucleic Acids Res 15, 2891 (1987).
Fornirsut et al. CRC Critical Reviews in Therapeutic Drug Carrier Systems vol. 2 Issue 2 (1984).

*Primary Examiner*—Esther L. Kepplinger
*Assistant Examiner*—Lora M. Green
*Attorney, Agent, or Firm*—Allegra J. Helfenstein

[57] ABSTRACT

The invention relates to microparticles incorporating a series of two or more fluorescent dyes having overlapping excitation and emission spectra allowing efficient energy transfer from the excitation wavelength of the first dye in the series, transfer through the dyes in the series and re-emitted as an optical signal at the emission wavelength of last dye in the series, resulting in a desired effective Stokes shift which is controlled through selection of appropriate dyes.

15 Claims, 3 Drawing Sheets

FLUORESCENT MICROPARTICLES WITH CONTROLLABLE ENHANCED STOKES SHIFT

FIELD OF THE INVENTION

The invention relates to polymeric materials incorporating multiple fluorescent dyes to allow for controlled enhancement of the Stokes shift. In particular, the invention describes microparticles incorporating a series of two or more fluorescent compounds having overlapping excitation and emission spectra, resulting in fluorescent microparticles with a desired effective Stokes shift. The novel fluorescent microparticles are useful in applications such as the detection and analysis of biomolecules, such as DNA and RNA, that require a very high sensitivity and in flow cytometric and microscopy analytical techniques.

BACKGROUND OF THE INVENTION

Microparticles labeled with fluorescent dyes have found use in a wide variety of applications. Microparticles are generally considered to be spherical or irregular in shape, and to be less than about 50 micrometers in diameter. They may be prepared by several practical methods from a variety of polymerizable monomers, including styrenes, acrylates and unsaturated chlorides, esters, acetates, amides and alcohols. Microparticles can be further modified by coating with one or more secondary polymers to alter the surface properties of the particles.

Fluorescent microparticles are most commonly used in applications that can benefit from use of monodisperse, chemically inert, biocompatible particles that emit detectable fluorescence and that can bind to a particular substance in the environment. For example, fluorescent particles to which biological molecules have been attached have been used for immunoassays (U.S. Pat. No. 4,808,524 (1989)), for nucleic acid detection and sequencing (Vener, et al. ANALYT. BIOCHEM. 198, 308 (1991); Kremsky, et al., NUCLEIC ACIDS RES. 15, 2891 (1987); Wolf, et al., NUCLEIC ACIDS RES. 15, 2911 (1987)), as labels for cell surface antigens, FLOW CYTOMETRY AND SORTING, ch. 20 (2$^{nd}$ ed. (1990)), and as tracer to study cellular metabolic processes (J. LEUCOCYTE BIOL. 45, 277 (1989)). The high surface area of microparticles provides an excellent matrix for attaching biological molecules while the fluorescent properties of these particles enable them to be detected with high sensitivity. They can be quantitated by their fluorescence either in aqueous suspension or when captured on membranes.

Fluorescent microparticles can be visualized with a variety of imaging techniques, including ordinary light or fluorescence microscopy and laser scanning confocal microscopy. Three-dimensional imaging resolution techniques in confocal microscopy utilize knowledge of the microscope's point spread function (image of a point source) to place out-of-focus light in its proper perspective. Small, uniform, fluorescently labeled polystyrene microspheres have been employed as point sources for these microscopes (Confocal Microscopy Handbook p. 154 (rev. ed. 1990)).

Many luminescent compounds are known to be suitable for imparting bright and visually attractive colors to various cast or molded plastics such as polystyrene and polymethyl methacrylate. Uniform fluorescent latex microspheres have been described in patents (U.S. Pat. No. 2,994,697, 1961; U.S. Pat. No. 3,096,333, 1963; Brit. U.s. Pat. No. 1,434,743, 1976) and in research literature (Molday, et al., J. CELL BIOL. 64, 75 (1975); Margel, et al., J. CELL SCI. 56, 157 (1982)). A recent patent application of the inventor (Brinkley, et al., Ser. No. 07/629,466, filed 12/18/90) describes derivatives of the dipyrrometheneboron difluoride family of compounds (derivatives of 4,4-difluoro-4-bora-3a,4a-diaza-s-indacene) as useful dyes for preparing fluorescent microparticles. This family of dyes possesses advantageous spectral data and other properties that result in superior fluorescent microparticles.

Figure 3A:
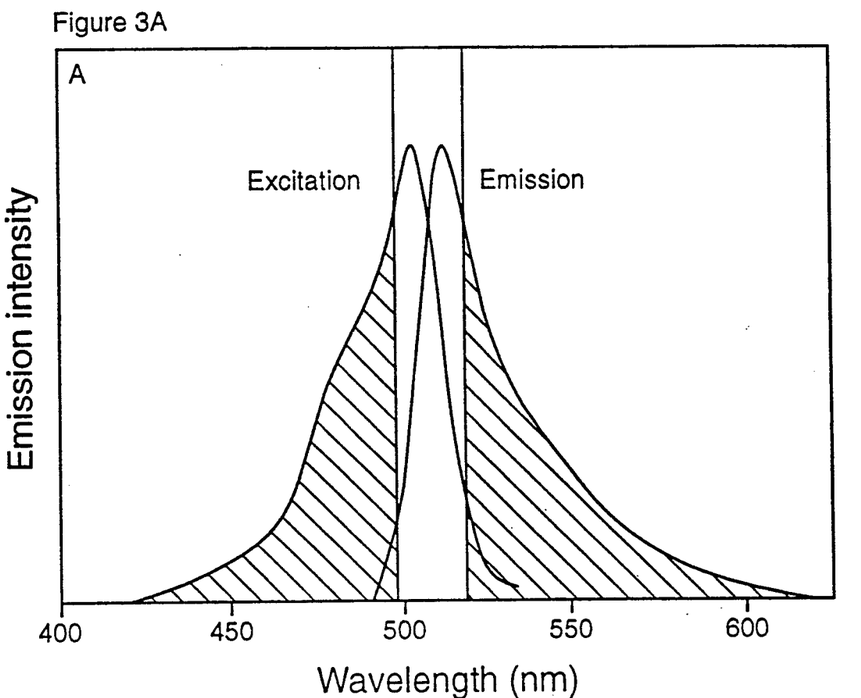
FIGS. 3A and B shows in graphic form the increase influorescent signal that is attainable by increasing the Stokes shift from about 10 nm to 70 nm in 0.093 micrometer latex microparticles. The microparticles in Spectrum A (FIG. 3A) contain 16 μMol/g-latex of Compound 1, while the microparticles in Spectrum B (FIG. 3B) contain 16 μMol/g-latex of Compound 1 (donor) and 9.6 μMol/g-latex of Compound 3 (acceptor). The relative shaded areas show the optimum filter bandwidths that can be used in each of these microparticle preparations, demonstrating the increasing signal that is obtainable from the microparticles containing the donor-acceptor dye pair.
Figure 3B:
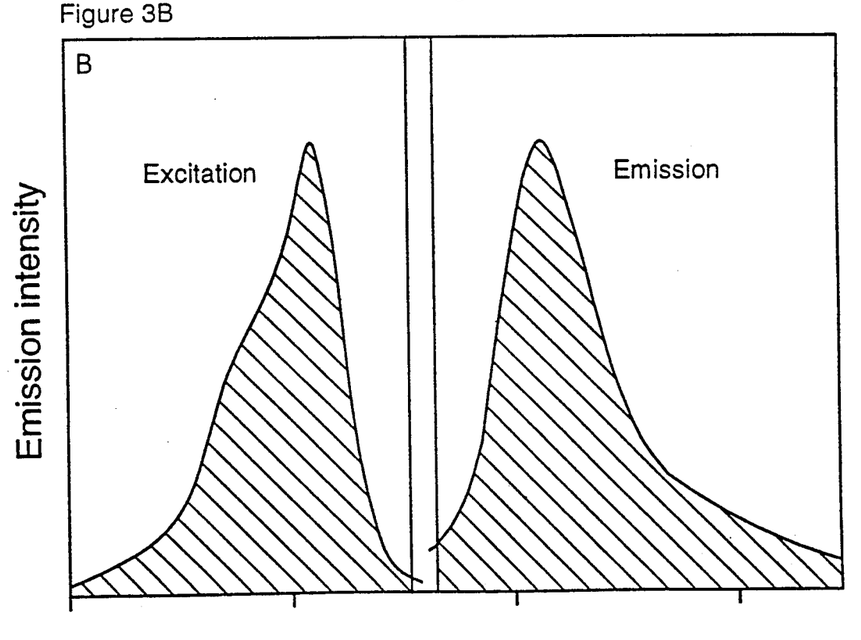

Although dipyrrometheneboron difluoride labeled materials are highly fluorescent and photochemically stable, a disadvantage of these fluorescent materials is their relatively small Stokes shift (the difference between the peak excitation and peak emission wavelengths) when only one dye is used. Because the optimum wavelength of the exciting light is close to the peak emission light, fluorescent particles with small Stokes shifts require precise excitation and emission filters to eliminate or reduce interference. The customary use of excitation filters blocks part of the excitation and emission light that would otherwise increase the efficiency of the fluorescence and reduces the intensity of the fluorescent signal. Fluorescent materials that incorporate bright fluorescent dyes with increased Stokes shifts would permit maximum utilization of the available excitation and emission light, resulting in a greater fluorescent signal (see e.g. FIGS. 3A and 3B).

Another advantage of fluorescent materials with large Stokes shifts is that they can be more easily detected in the presence of other fluorescent materials. Immunoassays are typically carried out in body fluids which contain many endogenous fluorescent molecules, such as bilins, flavins and drugs. Since the vast majority of interfering fluorescent materials have relatively short Stokes shifts, the use of a fluorescent label that emits at a wavelength far greater than its excitation wavelength makes the label easier to distinguish from background fluorescence, since its fluorescent signal is emitted at a wavelength at which most background fluorescence is minimal.

A third advantage of fluorescent materials with large Stokes shift is their usefulness in detecting multiple analytes in a single sample using a single excitation wavelength. Using two or more different fluorescent labels, each of which can be excited at a particular wavelength (e.g. the 488 nm argon laser principal emission), the emission peaks of the different labels are detected at different wavelengths, where each emission spectrum is characteristic of a single analyte. In order to successfully accomplish this, the emission peaks of the fluorescent labels must be well-separated from each other so the correction factors between the various dyes are minimized. High photostability of the label is also beneficial. Fluorescent materials with a large Stokes shift can be used in combination with fluorescent materials with a smaller Stokes shift where both materials excite at the same wavelength, but emit at different wavelengths, giving multiple signals that can be resolved using optical filters or monochromators.

Unfortunately, fluorescent compounds useful as labeling reagents that have Stokes shifts of 50–100 nm as well as high fluorescence efficiency and emission wavelengths of greater than 500 nm required for detectability are relatively rare. (Haugland, *Fluorescein Substitutes for Microscopy and Imaging*, OPTICAL MICROS- COPY FOR BIOLOGY pp. 143-57 (1990). The magnitude of the Stokes shift in fluorescent dyes has been found to be generally inversely proportional to the high absorbance needed to ensure a strong signal. Fluorescent dyes in use as labeling reagents for biological molecules, such as xanthenes, dipyrrometheneboron difluorides, rhodamines and carbocyanines commonly have Stokes shifts of less than about 30 nm.

The lack of suitable fluorescent dyes with large Stokes shifts has led to the development and use of protein-based fluorophores known as phycobiliproteins as labels (e.g. U.S. Pat. Nos. 4,520,110 and 4,542,104 both to Stryer, et al. (1985)). Like other fluorophores, they have been covalently attached to beads and macromolecules. See, e.g., Oi, et al., J. CELL BIO. 93,981 (1982). These large bilin-containing molecules have the desirable characteristics of very high extinction coefficients and they use internal energy transfer between unlike, covalently-linked fluorophores to accomplish a relatively large Stokes shift. They have the disadvantage of poor chemical stability, instability to photobleaching, limited long wavelength emission capability, bulky molecular size (MW > 100,000 Daltons) and relatively high cost. Furthermore, only a few proteins of this type are known and one cannot select or appreciably adjust their spectral properties. In an effort to improve the fluorescent emission efficiency of phycobiliproteins without significantly increasing their molecular size, phycobiliproteins have been covalently coupled to the fluorescent dye Azure A (U.S. Pat. No. 4,666,862 to Chan (1987)).

It is known that covalent coupling of a pair of fluorophores results in a fluorescent dye with a larger Stokes shift than either of the individual dyes (e.g. Gorelenko, et al., *Photonics of Bichromophores Based on Laser Dyes in Solutions and Polymers*, EXPERIMENTELLE TECHNIK DER PHYSIK 37, 343 (1989)). This approach, although reportedly effective in increasing the Stokes shift, requires complex synthetic procedures to chemically couple the two dyes together and are limited by the number and location of available reactive sites. The process of carrying out the necessary synthetic procedures to attach three, four, or more dyes sufficiently close together and in the proper configuration to undergo substantial energy transfer would be exceedingly difficult, if not impossible. Furthermore, covalently linked molecules typically have sufficient freedom of movement that significant collisional deactivation occurs, leading to loss of energy by vibrational relaxation rather than by fluorescence. There is a need for a way of combining the spectral properties of dyes by methods other than complex covalent coupling to provide useful fluorescent labels with an enhanced effective Stokes shift.

In studies of energy transfer between pairs of covalently linked dyes, it has been shown that the efficiency of energy transfer between two fluorescent dyes is inversely proportional to the sixth power of the distance between the two interacting molecules, consistent with Förster's theory (Stryer & Haugland, Energy Transfer: A Spectroscopic Ruler, PROC. NAT'L ACAD. SCI. USA 58, 719 (1967)). The reference suggests that the percentage of measurable energy transfer can be used to measure the distance separating the covalently linked fluorophores in the 10 to 60 Å range. A subsequent paper, Haugland, Yguerabide, & Stryer, *Dependence of the Kinetics of Singlet-Singlet Energy Transfer on Spectral Overlap*, PNAS 63, 23 (1969), reported that intramolecular singlet energy transfer depends on the magnitude of spectral overlap integral.

Energy transfer has been demonstrated between dyes that have been coupled to macromolecules to study intramolecular distances and conformation in biomolecules, e.g., Julien & Garel, BIOCHEM. 22, 3829 (1983); Wooley, et al., BIOPHYS. CHEM. 26, 367 (1987); and in polymer chains and networks, e.g. Ohmine, et al., MACROMOLECULES 10, 862 (1977); Drake, et al., SCIENCE 251, 1574 (1991). Energy transfer with resultant wavelength shifting has also been described for mixtures of dyes in lasing solutions, e.g. Saito, et al., APPL. PHYS. LETT. 56, 811 (1990). Energy transfer has been demonstrated between monomolecular layers of dyes and other organized molecular assemblies, e.g. Kuhn, *Production of Simple Organized Systems of Molecules*, PURE APPL. CHEM. 11, 345 (1966), abstracted in CHEM. ABSTRACTS 66, 671 (1967); Yamazaki, et al., J. PHYS. CHEM. 94, 516 (1990). Energy transfer between paired donor and acceptor dyes has also been demonstrated in polymer films as a way of studying the energy transfer dynamics, e.g. Mataga, et al., J. PHYS. CHEM. 73, 370 (1969); Bennett, J. CHEM. PHYSICS 41, 3037 (1964). Although the conformity of research results to Förster's theoretical formulation have been widely reported, utilitarian applications of the theory have been limited. The cited references neither anticipate nor suggest fluorescent microparticles incorporating a series of dyes to be used as labeling reagents with an enhanced effective Stokes shift.

It is an object of the invention to provide a more simple method than complex covalent coupling for combining the spectral properties of multiple dyes, while minimizing collisional deactivation, allowing efficient energy transfer and increasing the effective Stokes shift for the purpose of providing more useful fluorescent labeling reagents. It is a further object of the invention to provide materials that have not only an increased effective Stokes shift but materials for which the effective Stokes shift can be selectively controlled by the selection of appropriate dyes with overlapping spectral properties.

Immobilizing fluorescent dyes randomly in a polymeric matrix according to the subject invention provides just such a simple method of providing novel fluorescent materials with controllable, enhanced effective Stokes shifts. Certain fluorescent dyes, such as dipyrrometheneboron difluoride dyes, coumarin dyes and polyolefin dyes, have high fluorescence efficiency when incorporated into polymeric materials and are available in a large number of derivatives with a wide range of excitation and emission maxima, These characteristics allow the wavelength of excitation and the magnitude of the increase in the effective Stokes shift to be easily controlled by carefully selecting dyes with the appropriate spectral overlap for incorporation into the microparticles.

DESCRIPTION OF THE DRAWINGS

(acceptor), also excited at 490 nm; spectrum C is the emission of particles containing 9.6 μMol/g-latex of Compound 3, excited at 540 nm.

SUMMARY OF THE INVENTION

The invention relates to polymeric microparticles incorporating multiple fluorescent dyes to allow for controlled enhancement of the effective Stokes shift. The effective Stokes shift is the Stokes shift of the microparticle, i.e. the difference between the peak excitation wavelength of the initial donor dye and the peak emission wavelength of the ultimate acceptor dye after incorporation in the microparticle. In particular, the invention describes microparticles incorporating a series of two or more fluorescent compounds having overlapping excitation and emission spectra. Efficient energy transfer from the excitation wavelength of the first dye in the series which is re-emitted at the emission wavelength of last dye in the series results in a large and readily controllable effective Stokes shift. Selection of appropriate dyes results in fluorescent probes with desired excitation and/or emission wavelengths and preselected and increased effective Stokes shift.

Selection of Dyes

A series of fluorescent dyes is selected for incorporation into the microparticles based on their excitation and emission spectral properties. The dyes included in the series form a cascade of excitation energy transferred from high energy (short wavelength) to low energy (long wavelength) resulting in enhanced optical luminescence from the final dye in the series, regardless of the sequence of their incorporation or their random physical location in the microparticles.

The spectral properties for the series of fluorescent dyes should be determined in the polymeric materials in which they will be used. Although certain 4,4-difluoro-4-bora-3a,4a-diaza-s-indacene and 4,4-difluoro-4-bora-3a,4a,8-triaza-s-indacene dyes have been found to have spectral properties in polymer materials that are comparable to their spectral properties in solution, most dyes show significant and unpredictable spectral shifts depending on the media in which they are measured. Generally, oil soluble dyes and neutral dyes combine more readily with the polymeric materials. In addition to the desired excitation and emission peaks as described below, dyes useful for the invention also generally have a quantum yield of greater than about 0.2, preferably greater than about 0.5, as well as an extinction coefficient of greater than about 25,000 $cm^{-1}M^{-1}$, preferably greater than about 50,000 $cm^{-1}M^{-1}$.

The excitation and emission peaks and other spectral properties of candidate dyes are easily determined by conventional means. The excitation peak(s) of a dye can be approximately determined by running an absorption spectrum on any absorption spectrophotometer or, exactly, by running a fluorescent excitation spectrum using a scanning fluorescence spectrophotometer. The emission peak of the dye is also determined by using a fluorescence spectrophotometer to get an emission spectrum using a scanning fluorometer. Quantum yield is typically determined by measuring with a fluorometer the total fluorescence emission in the polymer of both the unknown dye and a reference dye with known absorbances at the excitation wavelength. The extinction coefficient is typically determined for a free dye in solution by using a spectrophotometer to measure absorbance of a solution with a gravimetrically determined concentration and calculating the extinction coefficient based on the Beer-Lambert law. After determining the spectral characteristics of likely dyes, dyes having the desired spectral characteristics are selected.

TABLE 1
CONVENTIONAL FLUORESCENCE EXCITATION SOURCES[a]

| Sources | Useful Wavelengths (nm) | Principal Lines (nm) |
|---|---|---|
| Mercury Arc | 250–600 | 254,366,436,546 |
| Xenon Arc | 250–1000 | 467, several > 800 |
| Tungsten Filament | 350–1000 | None |
| He—Cd Laser | 325,442 | 442 |
| Ar Laser | 350,360,458,476, 488,496,514 | 488,514 |
| He—Ne Laser | 543,594,633 | 633 |
| Kr Laser | 530,568,647,676 | 647 |
| Diode Laser | >650 | 850 (GaAlAs)[b] |

[a]Only primary excitation sources capable for continuous operation (CW) have been considered. Several other laser sources are available that either provide pulsed output (e.g. $N_2$ laser) or require pumping by CW ion lasers (e.g. dye lasers, Ti:Sapphire lasers).
[b]Material dependent, multiple types available.

The series of fluorescent dyes contains an initial donor dye with a desired excitation peak. The initial donor dye receives external excitation energy, such as from photons, x-rays, or decay of radioactive materials (e.g. β-emitters). In one embodiment of the invention, the initial donor dye receives excitation energy from incandescent or laser-based excitation sources to avoid the hazards of radioactive materials. Lasers, including argon ion, krypton ion, He-Cd, He-Ne, excimer, diode, metal vapor, neodymiumYAG, nitrogen and others, produce from one to several discrete lines that contain sufficient power for fluorescence excitation. Laser sources are available to provide many excitation lines over the spectrum from the UV to the infrared, to excite a wide range of fluorescent dyes.

The initial donor dye in the series has an excitation peak that overlaps the emission wavelength of energy from a preferred excitation source. For example, the most widely used beam-scanning confocal microscopes currently use air cooled Ar ion lasers, or more recently Ar-Kr gas mixes, allowing for fluorescent dye excitation between about 450 and 650 nm. Preferably, the excitation peak is optimal for absorption of energy from the excitation source, i.e. the excitation peak significantly overlaps the output of the excitation source.

Table 1 lists the wavelengths for a number of conventional excitation sources.

The series of fluorescent dyes used for the invention also has an ultimate acceptor dye with a desired emission peak. Generally, the desired emission peak is based on the magnitude of effective Stokes shift desired. The intensity of the fluorescence emission with respect to background "noise" (the signal-to-noise ratio), is fundamental to sensitivity and image contrast. The signal-to-noise quality of fluorescence data may be severely compromised by background signals at wavelengths different than the emitted fluorescence of interest. The background signals may result from light scatter or may be due to fluorescence intrinsically present in many biological systems or generated from an analytically useful second emitting species. It is possible, for example, to avoid cellular autofluorescence or to provide for a range of materials that can be excited by common wavelength but detected at different wavelengths by selection of a dye series that gives the desired effective Stokes shift.

Figure 1:
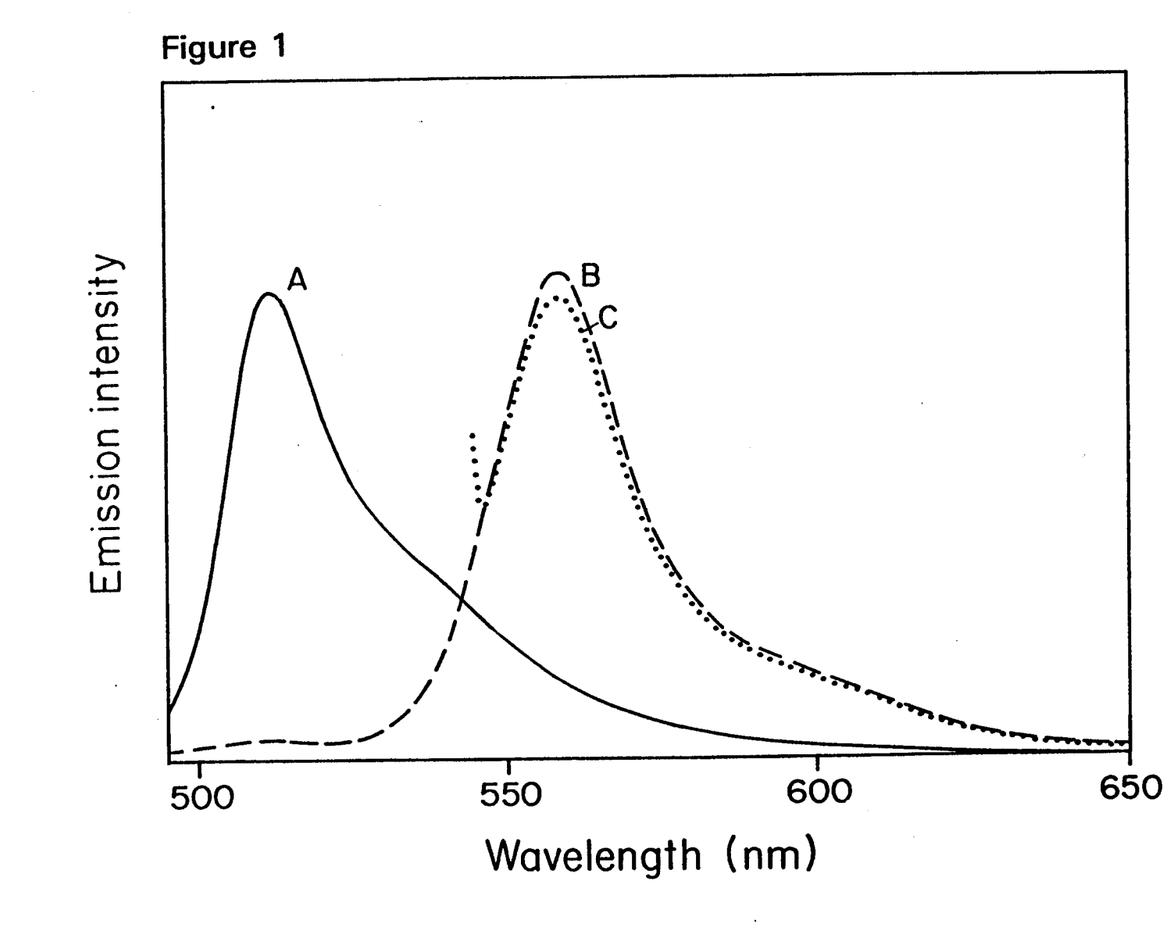
FIG. 1 is a graph of the emission spectra of 0.093 micrometer polystyrene latex particles containing various combinations of dipyrrometheneboron difluoride dyes. Spectrum A represents 16 μMol/g-latex of Compound 1 (see Table 2 below), exited at 490 nm (a preferred excitation wavelength); Spectrum B results from particles containing a mixture of 16 μMol/g-latex of Compound 1 (donor) and 9.6 μMol/g of Compound 3

The desired magnitude of effective Stokes shift may require that additional or "transfer" dyes be included in the series of fluorescent dyes to act as both intermediate donor and acceptor dyes. Individual dyes having a relatively narrow Stokes shift are preferred as transfer dyes for ease of exactly tailoring the desired excitation and emission peaks. Each transfer dye receives energy from the preceding dye in the series (acting as an acceptor dye with respect to the preceding dye) and substantially transfers the received energy to the next dye in the series (acting as a donor dye with respect to the next dye). Each dye in the series of fluorescent dyes has spectral overlap with the other dyes in the series, i.e. the emission peak of each donor or transfer dye in the series overlaps the excitation peak of the following acceptor or transfer dye in the series (Ex. 4/FIG. 2). The excitation and emission peaks overlap sufficiently so that, upon excitation, significant (i.e., greater than about 50%) transfer of the excitation energy from each dye to the next is achieved. The efficiency of energy transfer is measured by the loss in fluorescence intensity of the emission peak of the donor dye measured at the same degree of dye loading as polymer loaded with only the donor dye (FIG. 1). Typically, substantially complete energy transfer is achieved (i.e. greater than about 90%). Preferably, greater than about 95% energy transfer is achieved. More preferably, greater than about 98% energy transfer is achieved. Addition of a transfer dye is most appropriate when the efficiency of energy transfer falls below about 90%. The function of the transfer dye is to accept the excited state energy from the initially excited donor dye and to facilitate transfer of this energy to the ultimately detected acceptor dye.

Typically, the desired energy transfer is achieved when sufficient amounts of dyes are loaded into the polymeric microparticles so that the average intermolecular distance between donor and transfer and/or acceptor dyes is between about 40 Å and about 25 Å. Intermolecular distances between the dyes of greater than about 40 Å generally result in less efficient energy transfer, while intermolecular distances between the dyes of less than about 25 Å generally result in non-radiative energy loss that reduces the fluorescence emission of the dyes.

A sufficient number of donor, acceptor and transfer dyes are included in the series so that efficient energy transfer from the initial dye in the series to the ultimate dye in the series occurs. Although the dyes may be included in equal amounts, too much total dye may result in deterioration in properties of the polymer and in suboptimal fluorescence of the materials because of non-radiative energy loss. The average random distance between the fluorophores compatible with significant energy transfer generally results when the total dye concentration is less than about 10% (w/w); preferably the total dye concentration is between about 0.5 and 2% (w/w); more preferably between about 0.8 and 1.2% (w/w). Less (fewer molar equivalents) transfer dye than donor and acceptor dyes may sometimes be used to achieve the desired energy transfer. Less (fewer molar equivalents) ultimate acceptor dye than initial donor dye may also be effective in achieving the desired energy transfer. Increasing the amount of ultimate acceptor in proportion to the amount of initial donor generally has little effect on improving the ultimate fluorescent signal, whereas increasing the proportion of initial donor improves the effective extinction coefficient of and lead to greater emission from the ultimate acceptor dye. While not wishing to be bound by theory, it appears that the donor dye functions as a radiation collection mechanism for funneling energy output to the acceptor dye such that more initial donor dye results in more efficient absorption at excitation which in turn yields a more intense fluorescence signal. A workable ratio of initial donor dye to ultimate acceptor dye is between about 1:5 and about 10:1; preferably between about 1:1 and about 8:1; more preferably between about 4:1 and about 6:1.

In one embodiment of the invention, novel fluorescent materials are prepared from two or more polyazaindacene dyes (i.e. derivatives of 4,4-difluoro-4-bora-3a,4a-diaza-s-indacene or 4,4-difluoro-4-bora-3a,4a,8-triaza-s-indacene). Polyazaindacene derivatives suitable for preparation of fluorescent polymer microparticles according to this invention have the general structure of formula (I):

(I)

wherein $R_1$–$R_6$, which may be the same or different, are hydrogen, halogen, or alkyl, alkoxy, alkenyl, cycloalkyl, arylalkyl, acyl, or aryl, heteroaryl, alone or in combination; and $R_7$ is nitrogen, methine, or halogen-, alkyl-, alkoxy-, alkenyl-, cycloalkyl-, arylalkyl-, acyl-, aryl- or heteroaryl-substituted methine.

The alkyl, cycloalkyl, arylalkyl, acyl, alkoxy, and alkenyl substituents of the polyazaindacene derivatives generally each have independently fewer than about 20 carbon atoms, preferably fewer than about 10 carbon atoms. The term alkenyl includes ethenyl or conjugated dienyl or trienyl, which may be further substituted by hydrogen, halogen, alkyl, cycloalkyl, arylalkyl, acyl, (the alkyl portions of which each contain fewer than about 20 carbons), cyano, carboxylate ester, carboxamide, aryl or heteroaryl.

A heteroaryl group is a heterocyclic aromatic group that contains at least one heteroatom (a non-carbon atom forming the ring structure). The heteroaryl group can be a single ring structure or a fused two- or three-ring structure. Each ring can be a 5- or 6-member ring. The heteroaryl group can contain one or more heteroatoms. The term heteroaryl includes its alkyl-, aryl-, arylalkyl- or heteroaryl-substituted derivatives. For example, the heteroaryl substituent is pyrrole, thiophene, or furan (single ring, single heteroatom), or oxazole, isoxazole, oxadiazole, or imidazole (single ring, multiple heteroatoms). Alternatively, the heteroaryl group is a multi-ring structure containing one or more heteroatoms, for example, the heteroaryl substituent is benzoxazole, benzothiazole, or benzimidazole, (multi-ring, multiple heteroatoms), or benzofuran or indole (multi-ring, single heteroatom).

In general, 4,4-difluoro-4-bora-3a,4a-diaza-s-indacene derivative dyes are prepared from suitable pyrrole precursors, according to methods known in the art (e.g. U.S. Pat. No. 4,916,711 to Boyer, et al. (1990) and U.S. Pat. No. 4,774,339 to Haugland, et al. (1988) each of which are incorporated by reference). Typically, approximately stoichiometric proportions of pyrrole precursors, one of which contains an aldehyde or ketone function in the 2-position, are condensed in a reaction mediated by a suitable acid, such as hydrogen bromide, to yield an intermediate pyrromethene salt. Cyclization of the heterocyclic ring formation is completed by addition of boron trifluoride in combination with a strong base such as trimethylamine. Derivatives of 4,4-difluoro-4-bora-3a,4a,8-triaza-s-indacene are synthesized by the cyclization of azapyrromethenes with boron trifluoride in the presence of a base such as N,N-diisopropylethylamine. The azapyrromethene intermediates are prepared by the acid catalyzed condensation of 2-nitrosopyrrole derivatives with suitable pyrrole precursors having a hydrogen on the 2-position.

A representative sample of polyazaindacene dyes suitable for preparing fluorescent microparticles with controlled effective Stokes shifts and a summary of their spectral properties is included in Table 2. Other useful dipyrrometheneboron difluoride dyes are described in pending patents ser. no. 07/704,287 to Kang, et al., filed 5/22/91 and ser. no. 07/629,596 to Haugland, et al., filed 12/18/90 (each of which is incorporated by reference).

Appropriate selection of polyazaindacene derivatives, when incorporated together into a polymeric microparticle, have desired excitation and emission wavelengths that overlap sufficiently so that efficient transfer of energy from donor to acceptor is achieved, considering 1) the wavelength of the excitation and emission of the donor, transfer and/or acceptor dyes; 2) the overlap of the donor dye emission with the transfer and/or acceptor excitation; 3) relative concentrations of donor, transfer and/or acceptor dyes; and 4) the average distance between the dye molecules.

TABLE 2

Examples* of Polyazaindacene Dyes and Relevant Spectral Data

| Compound | $R_1$ | $R_2$ | $R_3$ | $R_4$ | $R_5$ | $R_6$ | $R_7$ |
|---|---|---|---|---|---|---|---|
| 1 | H | H | H | $CH_3$ | H | $CH_3$ | CH |
| 2 | $CH_3$ | H | $CH_3$ | $CH_3$ | H | $CH_3$ | CH |
| 3 | $CH_3$ | H | $CH_3$ | Ph | H | Ph | CH |
| 4 | Ph | H | Ph | Ph | H | Ph | CH |
| 5 | Ph | H | Ph | Ph | H | Ph | N |
| 6 | Ph | H | Ph | Pyr | H | H | CH |

*Representative, non-exclusive examples
2-pyrrolyl

| Compound | $\lambda^{Abs}_{max}$ (nm) | $\lambda^{Em}_{max}$ (nm) | $\lambda^{Abs}_{max}$ (nm) | $\lambda^{Em}_{max}$ (nm) |
|---|---|---|---|---|
| 1 | 490 | 509 | NA | NA |
| 2 | 505 | 515 | 504 | 512 |
| 3 | 528 | 548 | 540 | 557 |
| 4 | 564 | 591 | 578 | 605 |
| 5 | 644 | 668 | 650 | 679 |
| 6 | 606 | 633 | 625 | 645 |

Absorption maxima ($\lambda^{Abs}_{max}$) and emission maxima ($\lambda^{Em}_{max}$) measurements of free dye in methanol.
Absorption maxima ($\lambda^{Abs}_{max}$) and emission maxima ($\lambda^{Em}_{max}$) measurements of dye in aqueous suspension of latex. Optical density set at 0.1 at 700 nm.

Utilizing both the excitation and emission properties, the fluorescent materials are easily tailored to meet the specific requirements of the excitation source and the detector for a specific application. For example, Compound 1 may be selected as the donor dye as a dye having a very useful excitation of around 488 nm corresponding to the principle emission of argon lasers, with other dyes in Table 2 selected as transfer or acceptor dyes to yield a desired emission peak.

Figure 2:
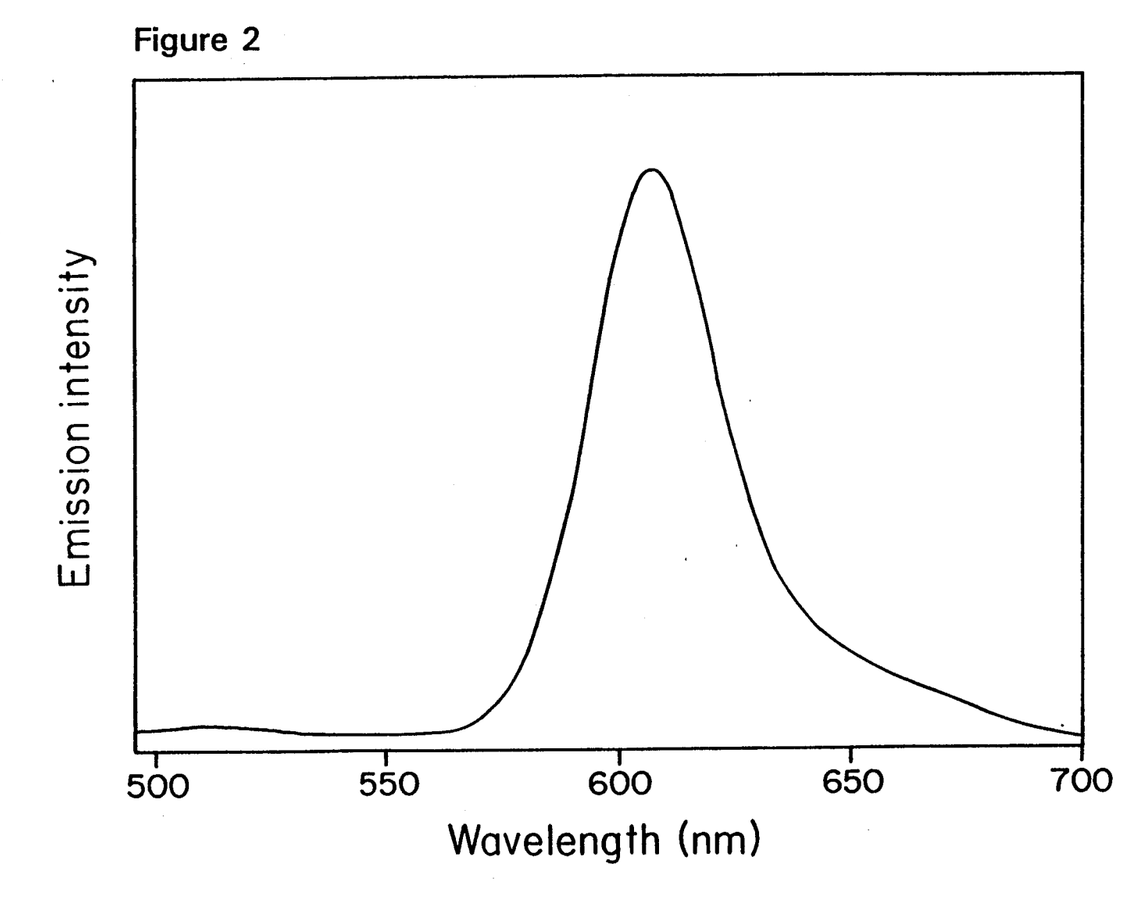
FIG. 2 shows the emission spectrum of 0.093 micrometer polystyrene latex particles containing three dipyrromethaneboron difluoride dyes; Compound 1 (donor dye), Compound 3, (transfer dye) and Compound 4 (acceptor) dye. The molar ratio of the dyes used to prepare the fluorescent latex microparticles was: 1 donor: 0.6 transfer: 0.9 acceptor.

Polystyrene microparticles labeled only with Compound 1 have maximum excitation at 504 nm and yellow-green fluorescence emission centered at about 512 nm. When the particles are labeled only with Compound 3, they have orange fluorescence emission centered at 557 nm. When Compound 1 (donor) and Compound 3 (acceptor) are combined in the appropriate molar ratios and incorporated into polystyrene microparticles (Ex. 3), the yellow-green emission of Compound 1 at 512 nm is transferred with greater than about 95% efficiency to Compound at 3, resulting in orange emission at 557 nm. The effective Stokes shift is increased from 8 nm to 56 nm (FIG. 1). Transfer dyes can be added to further increase the effective Stokes shift. When Compound 1 (donor), Compound 3 (transfer dye) and Compound 4 (acceptor) are combined in the appropriate molar ratios and incorporated into latex microparticles (Ex. 4), energy transfer (with greater than about 95% efficiency) results in red emission at 605 nm. The effective Stokes shift is increased from 8 nm to 101 nm (FIG. 2). When Compound 1 (initial donor), Compound 3 (transfer dye), Compound 4 (transfer dye) and Compound 6 (ultimate acceptor) are combined and incorporated into latex microparticles, energy transfer (with greater than about 90% efficiency) results in dark red emission at 645 nm. The effective Stokes shift is increased from 8 nm to 141 nm.

Alternatively, Compound 3 can be used as the donor and Compound 4 as the acceptor, resulting in latex particles that can be excited at about 530 nm and that emit at about 605 nm (an effective Stokes shift of about 75 nm), once again using the common argon laser (secondary line) but avoiding most of the autofluorescence of human serum. As long as there is spectral overlap between emission and excitation peaks of the dyes, many other dye combinations are possible.

In an another embodiment of the invention, the fluorescent dyes are a series of coumarin dyes. Suitable dyes include the commercially available dyes listed in Table 3. As with the polyazaindacene dyes previously described, an appropriate series of coumarin derivatives can be selected, which when incorporated together into a polymeric microparticle, have desired excitation and emission wavelengths that overlap sufficiently so that efficient transfer of energy from donor to acceptor is achieved. For example, when initial donor Coumarin 138 (7-Dimethylaminocyclopenta [c] coumarin), with excitation at 360 nm and emission centered at about 415 nm (in polystyrene latex) is combined in the appropriate molar ratio with ultimate acceptor Coumarin 314 (2,3,5,6-1H,4H-Tetrahydro-9-carboethoxyquinolizino-<9,9a,1-gh>coumarin), with absorption at 430 nm and emission centered at about 460 nm (in polystyrene latex) and incorporated into latex microparticles (Ex. 5), the blue emission of the Coumarin 138 is transferred to the Coumarin 314, resulting in blue-green emission centered at about 460 nm. The effective Stokes shift is increased from 55 nm to 100 nm.

The novel microparticles have very high fluorescence efficiency, typically with no apparent loss of signal intensity through the intermolecular energy transfer process. For example, excitation of the donor dye in the fluorescent microparticles illustrated in FIG. 1 at 490 nm, where the absorbance is 0.58 gives a signal at 557 nm that is equal to the corresponding signal at 557 nm resulting from excitation of the acceptor dye at 540 nm, where the absorbance is also 0.58. This extremely high efficiency of transfer is consistent with the observation that there is almost no emission signal detectable from the donor dye in the fluorescence spectrum of FIG. 1. Comparison of the integrated area of the emission signal of from 490 nm to 520 nm of Spectrum A, FIG. 1 with the integrated area of the emission signal from 490 nm to 520 nm of Spectrum B, FIG. 1 indicates that the transfer efficiency is about 99%.

The degree of overlap between the emission peak of the donor dye and the excitation peak of the transfer and/or acceptor dye(s) does not have to be complete. For example, in the microspheres described in FIG. 4, there is less than complete overlap between the emission peak of diphenylhexatriene (DPH) and the excitation peak of Compound 1. This overlap, nevertheless, results in transfer of about 75% of the emission from DPH to Compound 1.

Typically, the dyes are selected from the same family, such as the polyazaindacenes or coumarins described above. Other suitable families of dyes include hydrocarbon and substituted hydrocarbon dyes; scintillation dyes (usually oxazoles and oxadiazoles); aryl- and heteroaryl-substituted polyolefins ($C_2$–$C_8$ olefin portion); carbocyanines; phthalocyanines; oxazines; carbostyryl; and porphyrin dyes (see Table 3). It is also possible, however, to achieve efficient energy transfer between dyes that are structurally different such as between polyolefinic dyes and dipyrromethenboron difluoride dyes (Ex. 6); coumarin dyes and dipyrrometheneboron difluoride dyes (Ex. 7); polyolefinic dyes and coumarin dyes; dipyrrometheneboron difluoride dyes and oxazine dyes; and many others. Table 3 contains a partial list of commercially available, suitable fluorescent dyes.

Table 3. COMMERCIALLY AVAILABLE DYES

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'''-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'''-Dimethyl-p-quaterphenyl
2,2''-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethyl-benzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)-phenoxazonium Perchlorate
7-Ethylamino-6-methyl-4-trifluoromethylcoumarin
7-Ethylamino-4-trifluoromethylcoumarin
1,1',3,3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
N-Methyl-4-trifluoromethylpiperidino-<3,2-g>coumarin
3-(2'-N-Methylbenzimidazolyl)-7-N,N-diethylaminocoumarin
2-(1-Naphthyl)-5-phenyloxazole
2,2'-p-Phenylen-bis(5-phenyloxazole)
3,5,3'''',5''''-Tetra-t-butyl-p-sexiphenyl
3,5,3'''',5''''-Tetra-t-butyl-p-quinquephenyl
2,3,5,6-1H,4H-Tetrahydro-9-acetylquinolizino-<9,9a,1-gh>coumarin 2,3,5,6-1H,4H-Tetrahydro-9-carboethoxyquinolizino-<9,9a,1-gh>coumarin
2,3,5,6-1H,4H-Tetrahydro-8-methylquinolizino-<9,9a,1-gh>coumarin
2,3,5,6-1H,4H-Tetrahydro-9-(3-pyridyl)-quinolizino-<9,9a,1-gh>coumarin
2,3,5,6-1H,4H-Tetrahydro-8-trifluoromethyl-quinolizino-<9,9a,1-gh>coumarin
2,3,5,6-1H,4H-Tetrahydroquinolizino-<9,9a,1-gh>coumarin
3,3',2'',3'''-Tetramethyl-p-quaterphenyl
2,5,2'''',5''''-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene
Pyrene
Chrysene
Rubrene
Coronene
Phenanthrene
Fluorene
Aluminum phthalocyanine
Platinum octaethylporphyrin Once the spectral characteristics of a dye are determined in polymeric materials, as described above, those characteristics can be used to select the optimal dye series for a given application, taking into account the excitation source to be used, the available detection system, and the environment in which the materials will be used.

Incorporation Into Microparticle

After selection of the series of dyes with the desired spectral characteristics, the dyes are incorporated in a polymeric microparticle. The polymeric microparticle can be prepared from a variety of polymerizable monomers, including styrenes, acrylates and unsaturated chlorides, esters, acetates, amides and alcohols, including, but not limited to nitrocellulose, polystyrene (including high density polystyrene latexes such as brominated polystyrene), polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, and polydivinylbenzene.

In one embodiment of the invention, the novel fluorescent materials are prepared from undyed microparticles. The microparticles can be manufactured in a variety of useful sizes and shapes. They may be spherical or irregular in shape, and range in size from about 0.01 micrometers to about 50 micrometers. Typically, the labeled microparticles are less than about 15 micrometers in diameter and are spherical. More typically the microparticle is a microsphere less than about 5 micrometers in diameter. The microparticles may be of uniform size and/or shape or non-uniform. Alternatively, one or more dyes are added to pre-dyed microparticles such as the many varieties of fluorescent microspheres available commercially, provided that the requirement for spectral overlap between the resident dye and the additional dye(s) is met.

The fluorescent dyes are incorporated into the microparticles by any of the methods known in the art, such as copolymerization of a monomer and a dye-containing comonomer or addition of a suitable dye derivative in a suitable organic solvent to an aqueous suspension of polymer microparticles. For example, the fluorescent microparticles can be produced by free radical-initiated, anaerobic copolymerization of an aqueous suspension of a mono-unsaturated monomer that may or may not contain a covalent bonding group such as carboxyl, amino or hydroxyl and a fluorescent monomer mixture containing at least 10% by weight of monomers comprising the appropriate mixture of donor, transfer and/or acceptor dye moieties, according to the method of Rembaum (U.S. Pat. No. 4,326,008 (1982) incorporated by reference). The fluorescent microparticles can also be produced by gradual addition of a solution of the appropriate fluorescent dyes in an appropriate solvent to a stirred aqueous suspension of microparticles, as described by Bangs (UNIFORM LATEX PARTICLES (1984, Seragen, Inc.).

A major advantage of the subject microparticles is the ability to simply mix multiple transfer dyes with an initial donor dye and an ultimate acceptor dye to increase the effective Stokes shift of the microparticles and thus tailor the microparticles to meet specific applications. This cannot readily be accomplished by chemical means such as covalent attachment of the dyes to each other. In addition, the dyes are distributed throughout the particle, at concentrations that result in intermolecular separations that are smaller than can be practically attained by covalent chemical attachment, thus improving the likelihood of energy transfer. Furthermore, the dyes reside in a polymer that appears to restrict their free movement and prevent the dye molecules from vibrationally inactivating one another. Furthermore, incorporation of dyes in the polymeric microparticles usually increases their stability to illumination and protects the dyes from components in the medium surrounding the microparticles.

Oil-soluble fluorescent dyes, being freely soluble in organic solvents and very sparingly soluble in water, can easily be introduced by solvent-based addition of the dye to previously manufactured polymer microparticles. This offers the great advantage of being able to prepare uniform polymer microparticles with desired properties by carefully optimized procedures and then later adding the fluorescent dye series of choice. Furthermore, the solvent-based addition process gives great flexibility in adjusting the relative concentrations of the dyes, a key parameter in attaining efficient energy transfer.

In this manner, a large batch of microparticles with desired physical properties, such as size and charge density, can be prepared. Then various fluorescent dyes can be added to smaller portions of this batch resulting in subbatches of fluorescent polymer microparticles with desired effective Stokes shifts that give consistent and reproducible performance in applications such as development of diagnostic tests. In the case of fluorescent microparticles prepared by solvent-based addition of the dye to previously manufactured polymer microparticles, the surfaces properties of the subject fluorescent microparticles are not substantially different from the surface properties of the corresponding undyed microparticles. The fluorescent label in the microparticles is also not affected by changes in pH of the medium surrounding the microparticles.

Furthermore, the dyes used in the subject microparticles are not significantly removed from the microparticles by the water-based solvents that are commonly used as a suspension medium for the microparticles. For example, when aqueous suspensions of fluorescent microparticles containing Compound 4 and Compound 6 (Table 2) were subjected to temperatures of 60° C. in the presence of 0.2% sodium dodecyl sulfate, no detectable dye was extracted from the particles. When uniform microparticles are carefully prepared, the fluorescent microparticles are monodisperse in aqueous suspension. For example, 1.09 micrometer polystyrene microspheres dyed with Compound 1 and Compound 3 were shown to be monodisperse by visual observation (epifluorescence microscopy).

Additional Modification

The fluorescent compounds that are used to prepare the subject fluorescent polymer microparticles with large and controllable effective Stokes shift are generally lipophilic and commonly carry a net neutral charge, and therefore do not contribute to or alter the charged properties of the polymer microparticles as do other fluorescent dyes such as fluorescein and rhodamine 6G, that are commonly used to prepare fluorescent microparticles. As a result, the subject fluorescent microparticles can also include a variety of other substances in addition to the fluorescent dyes, such as bioreactive substances. Bioreactive substances are substances that react with or bind to molecules that are derived from a biological system, whether such molecules are naturally occurring or result from some external disturbance of the system (e.g. disease, poisoning, genetic manipulation). By way of illustration, bioreactive substances include biomolecules (i.e. molecules of biological origin including, without limitation, polymeric biomolecules such as peptides, proteins, polysaccharides, oligonucleotides, avidin, streptavidin, DNA and RNA, as well as non-polymeric biomolecules such as biotin and digoxigenin), microscopic organisms such as viruses, and haptens (such as hormones, vitamins, or drugs). Additional embodiments of the fluorescent microparticles include bioreactive substances covalently bound or passively adsorbed to the surface of the microparticles. The additional bioreactive substances are generally added according to methods generally known in the art, either covalently attached (e.g. CHEM. SOC. REV. 2, 249 (1973)) or non-covalently adsorbed (e.g. J. EXP. MED. 154, 1539 (1981)) to the surface of the fluorescent labeled microparticles. These surface-attached or adsorbed molecules are best added to the microparticles after the fluorescent dyes have been incorporated. These modifications, along with the controllable effective Stokes shifts make the subject microparticles useful in a wide variety of diagnostic tests.

In addition, the microparticles used to make the fluorescent microparticles can be prepared or purchased with a variety of surface properties, with functional groups including, but not limited to sulfate, phosphate, hydroxyl, carboxyl, ester, amide, amidine, amine, sulfhydryl and aldehyde. Surface groups are important for use in covalent or noncovalent binding of additional substances to the surface of the microparticles. The surface groups can also be selected to give the particles desired physical characteristics such as varying degrees of hydrophilicity.

Detection of Nucleic Acids

The subject fluorescent microparticles are ideal reagents for the detection of nucleic acids (e.g. RNA and DNA) by hybridization. The microparticles are relatively safe and non-toxic in comparison to radioactivity, which is the standard reagent used for such detection, yet the limits of detection with these microparticles rival those of radioactivity. They are chemically more stable than fluorophores currently in use and are easier to use than the reagents that require secondary detection through coupled enzymatic activity or antibodies. In addition, they can be coupled to antibodies for secondary detection, if signal enhancement is needed. Finally, because the novel microparticles can be tailored to emit at a variety of wavelengths, and have significant intensity at any of several selectable wavelengths, they can readily be used to do simultaneous or sequential multicolor detection of different nucleic acid species or different antigens.

Although the use of labeled microparticles to detect and identify nucleic acids is known (see references above), the subject microparticles have numerous advantages over others that have been described. Because of the long effective Stokes shift that can be achieved, it is possible to use the subject microparticles for applications where the intrinsic autofluorescence of the sample (as is present in algae or other plant cells, for example) or the presence of pigments (e.g. heme or xanthene) normally interferes with the signal. Furthermore, the subject microparticles can be prepared with modified surfaces that reduce non-specific binding. This characteristic enormously increases signal to background for any hybridization technique, allowing the use of standard hybridization filters as opposed to published protocols using labeled microparticles which require the use of a membrane with an unusually modified surface. Furthermore, the subject microparticles are significantly brighter than those currently available, resulting in detection limits up to orders of magnitude lower than is possible with any other labeled microparticles.

Nucleic acid detection generally involves probing a sample thought to contain target nucleic acids using a nucleic acid probe that contains a nucleic acid sequence that specifically recognizes the sequence of the target nucleic acids, such that the nucleic acid probe and the target nucleic acids in combination create a hybridization pair. The nucleic acid probe typically contains from greater than about 4 bases to as many as tens of thousands of bases, although probing entire chromosomes may involve millions of bases.

To provide a detection signal, one or more of the subject fluorescent microparticles are attached to the nucleic acid probe forming a microparticle-labeled probe. Alternatively, one or more nucleic acid probes may be attached to a single fluorescent microparticle. Attaching a nucleic acid probe to a microparticle is typically done using pairs of molecules that specifically recognize and bind tightly to one another, i.e. specific binding pair members (such as avidin and biotin or digoxigenin and anti-digoxigenin antibodies, for example). One member of the specific binding pair is coupled either directly (by incorporation during enzymatic or chemical synthesis or as a 5' or 3' end label) or through a linker molecule to the nucleic acid probe. The other member of the specific binding pair is coupled either directly or through a linker molecule to the fluorescent microparticle. Alternatively, the nucleic acid probe can be covalently linked to the fluorescent microparticle without the use of intervening specific binding pair members according to methods known in the art (e.g. Kremsky, et al., NUCLEIC ACIDS RES. 15, 2891 (1987) incorporated by reference).

It is a particular advantage of the subject microparticles that several microparticle-labeled probes can be prepared where all the probes have the same excitation peak of the initial donor dye but each probe has a different emission peak detectably distinct from the emission peaks of the other probes. As a result, these microparticles are particularly suited for the simultaneous detection of multiple nucleic acid species. Unlike radioactive methods, chemiluminescent labels or direct fluorophore conjugates, the subject microparticles can be made in a wide range of spectrally distinct colors that are simultaneously excitable with inexpensive, easily available equipment, such as hand-held uv lamps, and whose emission can be easily detected and distinguished by eye. Adding instrumental means for isolating the fluorescence signal tremendously expands the number of detectably different labels that are possible. Using the method of the instant invention, as many different labels can be made as can be resolved by appropriate choice of wavelength-selective elements such as filters, monochromators, or photodiode arrays, or other methods for discriminating fluorescent signals such as by pulse or phase-modulation techniques; each different label allowing the detection of a different analyte. Thus, having "X" detectably different dyes would allow X different nucleic acid probes to be labeled independently with different dyes and hybridized to a single nucleic acid target mixture, resulting in the detection of X independent target species in that mixture. For example, the presence of mycoplasma, viruses or plasmid species in the cytoplasm can be visibly distinguished from chromosomal or plasmid borne genes in the nucleus of a single cell (or in sections of a developing embryo), using in situ hybridization; or the presence of RNA or DNA molecules corresponding to as many as X different genes can be simultaneously assayed in Northern, Southern or spot blots or through solution hybridization; or the location of as many as X different genes could be determined with respect to one another on eucaryotic chromosomes on chromosome squashes or spreads, using in situ hybridization.

Formation of microparticle-labeled probes for such multicolor detection can be mediated in a variety of ways. These include a) direct nucleic acid-microparticle conjugates (with or without linker molecules), b) conjugation through the use of biotinylated nucleic acids and avidin labeled microparticles, or biotinylated nucleic acids, streptavidin, and biotinylated microparticles, c) digoxigenin labeled nucleic acids and antibodies to digoxigenin coupled to microparticles, d) nucleic acids labeled with other antigenic substances, such as fluorescein, or dinitrophenyl groups, detected with antibodies coupled to microparticles, or e) nucleic acids labeled with any antigenic substance, followed by reaction with the appropriate antibody, followed by detection with protein A coupled microparticles. These various detection techniques can also be combined to get multicolor detection that is multiply mediated.

The microparticle-labeled probes, whether for single or multicolor detection systems, are combined with a sample thought to contain target nucleic acids. Typically the sample is incubated with an aqueous suspension of the microparticle-labeled probes. Where a single color detection system is used the aqueous suspension contains substantially identical microparticle-labeled probes. Where a multicolor detection system is used, the aqueous suspension contains a number of detectably different microparticle-labeled probes. In each case, the microparticle-labeled probe is specific for a particular nucleic acid target or combination of nucleic acid targets.

Prior to combination with the microparticle-labeled probes, the sample is prepared in a way that makes the nucleic acids in the sample accessible to the probes. The sample may contain purified nucleic acids, either in mixtures or individual nucleic acid species; the sample may contain nucleic acids in lysed cells along with other cellular components; or the sample may contain nucleic acids in whole, permeabilized cells. Preparation of the sample will depend on the way the nucleic acids are available in the sample.

When the sample contains purified nucleic acids, the purified nucleic acids may be mixtures of different nucleic acids. Alternatively, the purified nucleic acids may be electrophoresed on agarose or polyacrylamide gels to provide individual nucleic acid species. Preparation of a sample containing purified nucleic acids comprises denaturation and neutralization. DNA may be denatured by incubation with base (such as sodium hydroxide) or heat. RNA is also denatured by heating (for spot blots) or by electrophoresing in the presence of denaturants such as urea, glyoxal, or formaldehyde, rather than through exposure to base (for Northern blots). The nucleic acids are then neutralized by the addition of an acid (e.g. hydrochloric acid), chilling, or addition of buffer (e.g. Tris, phosphate or citrate buffer), as appropriate.

Typically, the preparation of a sample containing purified nucleic acids further comprises immobilization of the nucleic acids on a solid support. Purified acids are generally spotted onto filter membranes such as nitrocellulose filters or nylon membranes in the presence of appropriate salts (such as sodium chloride or ammonium acetate) for DNA spot blots. Alternatively, the purified nucleic acids are transferred to nitrocellulose filters by capillary blotting or electroblotting under appropriate buffer conditions (for Southern blots). To permanently bind nucleic acids to the filter membranes, standard crosslinking techniques are used (for example, nitrocellulose filters are baked at 80° C. in vacuo; nylon membranes are subjected to illumination with 360 nm light). The filter membranes are then incubated with solutions designed to prevent non-specific binding of the nucleic acid probe (such as BSA, casein hydrolysate, single-stranded nucleic acids from a species not related to the probe, etc.) and hybridized to probes in a similar solution. Non-specifically bound probe is washed from the filters with a solution such as saline citrate or phosphate buffer. Filters are blocked with agents to prevent non-specific adherence of microparticles (such as detergent). Finally, samples are probed with labeled microparticles and non-specifically bound microparticles are removed by washing with more blocking buffer.

When the sample contains cellular nucleic acids (such as chromosomal or plasmid borne genes within cells, RNA or DNA viruses or mycoplasma infecting cells, or intracellular RNA), preparation of the sample involves lysing or permeabilizing the cell, in addition to the denaturation and neutralization already described. Cells are lysed by exposure to agents such as detergent (for example sodium dodecyl sulfate, Tween, sarkosyl or Triton), lysozyme, base (for example sodium, lithium or potassium hydroxide), chloroform, or heat. Cells are permeabilized by conventional methods, such as by formaldehyde in buffer.

As with samples containing purified nucleic acids, preparation of the sample containing cellular necleic acids typically further comprises immobilization of the nucleic acids on a solid support. In lysed cells, cells in suspension are spotted onto or filtered through nitrocellulose or nylon membranes, or colonies of cells are grown directly on membranes that are in contact with appropriate growth media, and the nucleic acids are permanently bound to filters as described above. Permeabilized cells are typically fixed on microscope slides with known techniques used for in situ hybridization and hybridization to chromosome "squashes" and "spreads," (e.g. with a reagent such as formaldehyde in a buffered solution). Slides are then treated with a solution (such as triethanolamine and acetic anhydride) to block non-specific binding of the microparticles and treated with a buffering solution (such as Tris/glycine, phosphate buffered saline, or saline citrate). Finally, samples are dehydrated to prepare them for microscopy (with reagents such as a graded series of ethanol dilutions) and dried. Prehybridization and hybridization solutions, blocking, probing and washing on the solid support are essentially as described above.

Following the probing of the sample with the microparticle-labeled probes, unbound probes are removed from the sample by conventional methods such as washing. The sample is then illuminated with a source of excitation energy emitting within the range of the excitation peak of the initial donor dye of the microparticle-labeled probes, after which fluorescence resulting from the illuminated probes is detected.

The following illustrations describe the practice of the invention and are by way of example and not by way of limitation.

EXAMPLE 1

Preparation of 4,4-Difluoro-5,7-diphenyl-3-(pyrrol-2-yl)-4-bora-3a,4a-diaza-sindacene (Compound 6)

To a solution of 90 mg (0.36 mmol) of 3,5-diphenyl-pyrrole-2-carboxaldehyde and 50 mg (0.37 mmol) of 2,2'-bipyrrole in 15 mL of dichloromethane is added 40 $\mu$L (0.45 mmol) of phosphorus oxychloride. The reaction mixture is stirred at room temperature for 12 hours and is added 225 $\mu$L (1.62 mmol) of N,N-diisopropylethylamine, followed by addition of 200 $\mu$L (1.62 mmol) of boron trifluoride etherate. After the whole mixture is stirred at room temperature for 2 hours, it is washed with two 20 mL portions of water. The organic layer is separated, dried over anhydrous sodium sulfate and concentrated under reduced pressure to give a dark purple-blue solid. The crude product is purified by chromatography on silica gel with 30% chloroform in hexane as eluant to give 49 mg (33%) of a dark purple-blue solid.

2,2'-Bipyrrole is prepared as described in H. Rapoport et al., J. AM. CHEM. SOC. 84, 2178 (1962). 3,5-Diphenyl-2-pyrrolecarboxaldehyde is prepared from 2,4-diphenylpyrrole by the Vilsmeyer Haak formylation, according to R. M. Silverstein et al., ORG. SYNTH. COLL. Vol. IV, p. 831.

Compounds 1 and 2 are prepared by the reaction of pyrrole-2-carboxaldehyde and 3,5-dimethylpyrrole-2-carboxaldehyde, respectively with 2,4-dimethylpyrrole as described in EXAMPLE 1. Compounds 3 and 4 are prepared by the reaction of 2,4-dimethylpyrrole and 2,4-diphenylpyrrole, respectively, with 3,5-diphenyl-pyrrole-2-carboxaldehyde as described in EXAMPLE 1.

EXAMPLE 2

Preparation of 4,4-Difluoro-1,3,5,7-tetraphenyl-4-bora-3a,4a,8-triaza-s-indacene (Compound 5)

A mixture of 85 mg (0.40 mmol) of 2,4-diphenylpyrrole and 100 mg (0.40 mmol) of 2-nitroso-3,5-diphenyl-pyrrole in 5 mL of glacial acetic acid is heated under reflux for 3 hours. After the reaction mixture is cooled to room temperature, it is poured into 20 mL of ether. The resulting precipitate is collected by filtration, washed with ether and dried to give a 89 mg of a blue solid. This solid is dissolved on 10 mL of dichloromethane and are added 100 $\mu$L (0.57 mmol) of N,N-diisopropylethylamine and 70 $\mu$L (0.51 mmol) of boron trifluoride etherate. After the reaction mixture is stirred at room temperature for 2 hours, it is worked-up and purified in a similar way as described in EXAMPLE 1 to give a 80 mg (40%) of Compound 5 as a dark blue solid.

EXAMPLE 3

Preparation of Novel Microparticles Using Two Polyazaindacene Dyes

To a vigorously stirred 200 mL suspension 0.093 micrometer carboxylate-modified latex (Interfacial Dynamics Corp., Portland, Oreg.; 3.05% solids in 50% v/v distilled water/methanol) is added a solution of 50 mg of Compound 1 and 17 mg of Compound 3 dissolved in a homogeneous mixture of 9 mL of dichloromethane and 16 mL of absolute ethanol. The addition of the dye is carried out by means of a syringe pump fitted with a Teflon delivery tube (0.038 in i.d.) and the dye solution is delivered at a flow rate of 6 mL/hr. After addition is complete, the suspension is filtered through loosely packed glass wool to remove any debris and then partially evaporated at room temperature on a rotary evaporator to remove the dichloromethane and alcohols. The aqueous suspension of dyed latex is then filtered again through glass wool to remove any additional debris and dialyzed (25 mm tubing, MW cutoff 12,000-14,000) to remove any residual dye. The dialysis is carried out until no more free dye is removed from the particles as detected by fluorimetric analysis of the dialysate. The fluorescent latex suspension is removed from dialysis and filtered again through glass wool to remove any remaining aggregates and other debris. The suspension is then sonicated in a bath sonicator for 10 minutes to ensure monodispersity. Visual analysis of a dilute aqueous suspension of the product by fluorescence microscopy using standard rhodamine filters shows uniformly dyed particles that are highly monodisperse. Spectral analysis of the product, exciting at 480 nm shows a single emission peak centered at 557 nm.

EXAMPLE 4

Preparation of Novel Microparticles Using Three Polyazaindacene Dyes

To a vigorously stirred 200 mL suspension 0.030 micrometer carboxylate-modified latex (Interfacial Dynamics Corp., Portland, Oreg.; 3.67% solids in 50% v/v distilled water/methanol) is added a solution of 50 mg of Compound 1, 17 mg of Compound 3 and 22 mg of Compound 4 dissolved in a homogeneous mixture of 7.5 mL of dichloromethane and 17.5 mL of absolute ethanol. The addition of the dye and purification of the product is carried out as described in EXAMPLE 3. Visual analysis of a dilute aqueous suspension of the product by fluorescence microscopy using standard Texas Red compatible filters shows uniformly dyed particles that are highly monodisperse. Spectral analysis of the product, exciting at 480 nm shows a single emission peak centered at 605 nm.

EXAMPLE 5

Preparation of Novel Microparticles Using Two Coumarin Dyes

To a vigorously stirred 200 mL suspension 0.282 micrometer carboxylate-modified latex (Interfacial Dynamics Corp., Portland, Oreg.; 2.75% solids in 50% v/v distilled water/methanol) is added a solution of 30 mg of Coumarin 138 (Eastman Kodak, Rochester, N.Y.) and 30 mg of Coumarin 314 (Eastman Kodak) dissolved in a homogeneous mixture of 7.5 mL of dichloromethane and 17.5 mL of absolute ethanol. The addition of the dye and purification of the product is carried out as described in EXAMPLE 3. Visual analysis of a dilute aqueous suspension of the product by fluorescence microscopy using standard AMCA excitation and emission filters shows uniformly dyed particles that are highly monodisperse. Spectral analysis of the product, exciting at 360 nm shows an emission peak centered at 410 nm and an emission peak centered at 460 nm. The integrated ratio of the 460 nm peak (from coumarin 314) to the 410 peak (from coumarin 138) is 92:8, indicating efficient transfer of emission energy from coumarin 138 to coumarin 314.

EXAMPLE 6

Preparation of Novel Microparticles Using One Polyolefin Dye and One Polyazaindacene Dye To a vigorously stirred 200 ml suspension 0.977 micrometer carboxylate-modified latex (Interfacial Dynamics Corp., Portland, Oreg.; 2.10% solids in 50% v/v distilled water/methanol) is added a solution of 50 mg of diphenylhexatriene (DPH) and 10 mg of Compound 1 dissolved in a homogeneous mixture of 9 mL of dichloromethane and 16 mL of absolute ethanol. The addition of the dye and purification of the product is carried out as described in EXAMPLE 3. Visual analysis of a dilute aqueous suspension of the product by fluorescence microscopy using standard fluorescein filters shows uniformly dyed particles that are highly monodisperse. Spectral analysis of the product, exciting at 365 nm shows an emission peak centered at 430 nm and a second emission peak centered at 512 nm. The integrated ratio of the 430 nm peak (from DPH) to the 512 peak (from Compound 1) is 74:26, indicating efficient transfer of emission energy from DPH to Compound 1. As a further confirmation of the effectiveness of the energy transfer, 0.093 micron latex particles are prepared as described above with 10 mg of Compound 1 only. When these latex particles are excited at 365 nm under the same conditions as the particles containing both DPH and Compound 1, the integrated area of the 512 nm peak is less than 10% of that obtained in the two dye system.

EXAMPLE 7

Preparation of Novel Microparticles Using One Coumarin Dye and One Polyazaindacene Dye To a vigorously stirred 200 mL suspension 0.282 micrometer carboxylate-modified latex (Interfacial Dynamics Corp., Portland, Oreg.; 2.10% solids in 50% v/v distilled water/methanol) is added a solution of 50 mg of coumarin 6 and 50 mg of Compound 1 dissolved in a homogeneous mixture of 9 mL of dichloromethane and 16 mL of absolute ethanol. The addition of the dye and purification of the product is carried out as described in EXAMPLE 3. Visual analysis of a dilute aqueous suspension of the product by fluorescence microscopy using standard fluorescein excitation and emission filters shows uniformly dyed particles that are highly monodisperse. Spectral analysis of the product, exciting at 430 nm shows the major emission peak to be centered at 512 nm. There is a smaller emission peak centered at 520 nm from the coumarin 6, indicating substantial, but not complete energy transfer.

EXAMPLE 8

Preparation of Avidin-Labeled Novel Microparticles Using Two Polyazaindacene Dyes To a 15 mL glass centrifuge tube is added 2 mL 15 mM sodium acetate buffer, pH 5.0; 4 mg of avidin (allow to completely dissolve); and 5 mL of a 2% aqueous suspension of the latex microspheres prepared in EXAMPLE 6. The mixture is agitated and incubated at room temperature for 15 minutes. Then 40 mg of 1-ethyl-3-(dimethylaminopropyl)carbodiimide (EDAC) is added and the tube is agitated to mix the contents. The pH is adjusted to $6.5 \pm 0.2$ with dilute NaOH and the reaction mixture is incubated with gentle mixing on a rocker or orbital shaker for 2 hours at room temperature. The avidin-labeled latex microspheres are separated from unbound avidin by centrifugation at 2,000 RPM for 20 minutes. The supernatant is decanted and the avidin-labeled latex pellet is resuspended in 100 mM PBS, pH 7.4 and washed 3 times by centrifugation/decantation. The avidin-labeled latex is suspended in a final volume of 5 mL of 100 mM PBS, pH 7.4.

Biotinylated latex microspheres are prepared according to the procedure of EXAMPLE 8 using BSA conjugated to 6-((6-((biotinoyl)amino)hexanoyl)amino)hexanoic acid in place of avidin.

EXAMPLE 9

Detection of M13 DNA Spotted onto Nitrocellulose Filters Using Novel Microparticles.

Nitrocellulose filters (BA 85, 0.45 micron pores, Schleicher and Schuell, Keene, NH) are pretreated by incubation with water, then 20X SSC (175 g NaCl, 88 g sodium citrate, pH 7.0, per liter) and air dried. M13 single-stranded DNA is diluted serially in T.E. (10 mM Tris-Cl, pH 7.8, 1 mM EDTA) in microfuge tubes and spotted onto these filters. Filters are air dried, then baked 1 hour, 80° C., in a vacuum oven. Prehybridization is done by incubation in 6X SSC (52.5 g NaCl, 26.4 g sodium citrate, pH 7.0 per liter), 0.5% sodium dodecyl sulfate (SDS), 5X Denhardt's (0.1% Ficoll, 0.1% polyvinylpyrrolidone, 0.1% bovine serum albumin (BSA)) and 100 micrograms/ml single stranded DNA, 1 hour, at 60° C. Hybridization is done in the same solution with the addition of 30 ng/ml M13 biotinylated oligonucleotide probe at the same temperature for 3 hours. The filters are washed by incubation in 6X SSC, 0.1% SDS for 20 minutes at room temperature and then for 5 minutes at 60° C. Filters are then blocked by incubation in 100 mM Tris, 150 mM NaCl, pH 7.8, 0.05% non-fat dried milk, 0.5% Tween-20 for 1 hour. Labeling is done by incubation at room temperature for 1 hour in the same solution containing a 1:1000 dilution of the microparticles prepared in EXAMPLE 8 (2% solids), which are avidin conjugated and fluorescently labeled. Finally, non-specifically adsorbed microparticles are removed by washing filters in the same solution without non-fat dried milk, for 10 minutes, at room temperature. Spots are visualized by illumination with 360 nm light.

EXAMPLE 10

Detection of LacZ Gene Specific mRNA in Lysed Tissue Culture Cells Using Novel Microparticles.

A suspension of $1 \times 10^4$ CREBAG (positive for the lacZ gene) or NIH3T3 cells (negative for the lacZ gene) is spotted onto nitrocellulose filters (BA85, 0.45 micron pores, Schleicher and Schuell, Keene, N.H.). The cells are lysed by incubation with 100 mM NaCl, 10 mM Tris-Cl, pH 7.8, 25 mM EDTA and 0.5% sodium dodecyl sulfate (SDS). The DNA is denatured by incubation with 1.5 M NaCl, 0.5 minutes, then neutralized by incubation for 5 minutes with 100 mM Tris-Cl, pH 7.8, 150 mM NaCl. The filters are baked 1 hour at 80° C. in a vacuum oven. Filters are then prehybridized by incubation with 6X SSC, 5X Denhardt's, 0.5% SDS, and 100 micrograms/ml salmon sperm DNA for 1 hour at 60° C. Hybridization is done in the same solution, with the addition of 30 ng/ml biotinylated M13 oligonucleotide probe (which hybridizes to the lacZ gene), incubated for 1 hour at 60° C. Filters are washed with 6X SSC containing 0.1% SDS for 20 minutes at room temperature, then in the same solution for 5 minutes at 60° C. The filters are then blocked to prevent non-specific binding of the microparticles by incubation with 100 mM Tris-Cl, pH 7.8, 150 mM NaCl, 0.5% Tween-20 and 3% w/v bovine serum albumin (BSA) for 1 hour at room temperature. The microparticles prepared in EXAMPLE 8 (biotinylated, fluorescently labelled microparticles, 2% solids) are added in a final dilution of 1:1000 to the blocking buffer and incubated with the filters for 30 minutes at room temperature. Filters are then washed with 100 mM Tris, pH 7.8, 150 mM NaCl for 30 minutes at room temperature and the signal visualized by irradiation with a hand-held UV lamp (UVP, Inc., San Gabriel, Calif.) with a broad-bandwidth filter centered at about 360 nm. The CREBAG cells show clearly visible yellow-green fluorescence while the NIH3T3 cells do not.

EXAMPLE 11

Detection of LacZ Gene Specific mRNA by In Situ Hybridization Using Novel Microparticles.

CREBAG (lacZ positive) or NIH3T3 (lacZ negative) cells growing on a microscope slide are permeabilized and fixed by incubation for 15 minutes in 3.7% formaldehyde in PBS (8 g sodium chloride, 0.2 g KCl, 1.44 g $Na_2HPO_4$, 0.24 g $KH_2PO_4$, pH 7.4, per liter). Slides are rinsed twice in 2X SSC (17.5 g sodium chloride, 8.8 g sodium citrate, pH 7.0, per liter) for 1 minute, then incubated for 10 minutes 0.1M triethanol amine/0.25% acetic anhydride. Cells are then equilibrated for 1 minute in 2X SSC, for 1 minute in PBS, and for 30 minutes in 0.1M Tris/glycine buffer, pH 7.0. Slides are rinsed twice in 2X SSC, then dehydrated in 70% and 95% ethanol then air dried. Prehybridization is done by incubation of each slide with 300 microliters of a solution containing 50% formamide, 5X Denhardt's (0.1% Ficoll, 0.1% polyvinylpyrrolidone, 0.1% bovine serum albumin (BSA)), 6X SSPE (1.08M sodium chloride, 60M $NaH_2PO_4$, pH 7.4, 6 mM EDTA), 250 micrograms/ml *E. coli* tRNA, 500 micrograms/ml calf thymus DNA for 1 hour at room temperature. Hybridization is done using the same volume of the same solution with the addition of 2 micrograms/ml biotinylated oligonucleotide probe and incubated overnight at 42° C. Filters are then washed several times with 2X SSC, blocked by incubation with PBS containing 3% BSA and 0.1% Tween 20 and incubated with a 1:1000 dilution of microparticles as prepared in EXAMPLE 8 above (avidin labeled fluorescent microparticles, 2% solids) for 30 minutes at room temperature. Slides are washed briefly with PBS and visualized. Viewed with a microscope with a UV light source, the CREBAG cells show easily detectable green fluorescence while the NIH3T3 cells do not.

EXAMPLE 12

Detection of Developmentally Important mRNA Molecules in Zebrafish Embryos by Northern Blotting Using Novel Microparticles Microparticles are directly conjugated to oligonucleotide probes directed against the zebrafish engrailed, inverted and HOX (homebox) genes, as well as the CAT (chloromphenical acetyl transferase) gene, using any one of the methods described in the literature. The oligonucleotide probes are each conjugated to differently labeled 0.1 micron microparticles: engrailed to yellow green (emission 512 nm, latex incorporating Compound 1), inverted to orange (emission 557 nm, latex incorporating Compounds 1 & 3 as in Example 3), HOX to red (emission 605 nm, latex incorporating Compounds 1, 3 & 4, as in Example 4) and CAT to crimson (emission 650 nm, latex incorporating Compounds 1, 3, 4 & 6). Total cellular RNA is prepared from zebrafish embryos at several different stages of development. RNA is prepared by cellular disruption (using a baked glass homogenizer, in the presence of homogenization buffer, consisting of 50 mM NaCl, 50 mM Tris-Cl, pH 7.5, 5 mM EDTA, 0.5% sodium dodecyl sulfate (SDS), and 200 micrograms/ml proteinase K) and incubated for 1 hour at 37° C. to digest proteins. The homogenate is extracted with an equal volume of phenol:chloroform, 1:1, and the aqueous phase reextracted twice more with the same solution. The nucleic acids are precipitated by the addition of 0.1 volume of 3M sodium acetate (pH 5.2) and 2.5 volumes of ice cold ethanol, incubated 2 hours on ice. Nucleic acids are pelleted by centrifugation at 5000 g for 15 minutes at 4° C., the supernatant is discarded, and the pellet allowed to air dry. Total nucleic acids (consisting mainly of RNA) are dissolved in sterile water.

10 micrograms of RNA per lane is glyoxylated using standard methods and electrophoresed on an agarose gel (1% agarose in 0.01M sodium phosphate, pH 7.9). The RNA is subjected to capillary transfer in 20X SSPE (174 g NaCl, 27.6 g $NaH_2PO_4.H_2O$ and 7.4 g EDTA, pH 7.4, per liter) to a nitrocellulose filter membrane (BA85, 0.45 micron pores, Schleicher and Schuell, Keene, N.H.) that is pre-equilibrated in 2X SSC (17.5 g NaCl, 8.8 sodium citrate, pH 7.0 per liter). The nitrocellulose filter membrane is baked for 1 hour at 80° C., in a vacuum oven to permanently bind nucleic acids. The blot is then prehybridized by incubation with 6X SSC (52.5 g NaCl, 26.4 g sodium citrate, pH 7.0, per liter), 0.5% SDS, 5X Denhardt's (0.1% Ficoll, 0.1% polyvinylpyrrolidone, 0.1% bovine serum albumin (BSA)), 0.05% non-fat dried milk, 0.5% Tween-20 and 100 micrograms/ml single stranded DNA for 1 hour at 60° C. The filters are then hybridized in the same solution, with the addition of 30 ng/ml of each microparticle-conjugated oligonucleotide probe, at the same temperature, for 3 hours. The filters are then washed with 6X SSC, 0.1% SDS for 20 minutes at room temperature and then for 5 minutes at 60° C. to remove non-specifically adsorbed probe. Bands corresponding to individual RNA species are visualized by illumination with a hand-held uv light source (UVP, Inc., San Gabriel, Calif.) with a broad bandwidth filter centered at about 360 nm. Each RNA species shows a distinct color, showing that RNA corresponding to the CAT gene is produced at all stages during development, while RNAs corresponding to engrailed, HOX and inverted genes are only present at defined periods during development.

It is to be understood that, while the foregoing invention has been described in detail by way of illustration and example, only the preferred or specific embodiments have been revealed, and that numerous modifications, substitutions, and alterations are all permissible without departing from the spirit or scope of the invention as described in the following claims.

What is claimed is:

1. A fluorescent microparticle made by the process comprising: a) selecting a series of dyes comprising an initial donor dye with a desired excitation peak and a final acceptor dye with a desired emission peak, wherein the desired excitation peak and the desired emission peak are determined in a polymeric material, and wherein said polymeric material is made up of polymerizable monomers, and wherein each dye in the series has a spectral overlap sufficient to allow for significant energy transfer of excitation energy to the final acceptor dye, b) incorporating said series of dyes in a polymeric microparticle comprising said polymeric material, wherein said series of dyes are randomly incorporated into said polymeric microparticle.

2. A microparticle, as claimed in claim 1, wherein the spectral overlap allows for energy transfer that is greater than about 90%.

3. A microparticle, as claimed in claim 1, wherein the polymeric microparticle is polystyrene, brominated polystyrene, polyacrylic acid, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, or polydivinylbenzene.

4. A microparticle, as claimed in claim 1, wherein the fluorescent dyes are polyazaindacene; coumarin; oxazole or oxadiazole; aryl- or heteroaryl-substituted polyolefin wherein the olefin portion has 2-8 carbons; carbocyanine; phthalocyanine; oxazine; carbostyryl; or porphyrin dyes; or combinations thereof.

5. A microparticle, as claimed in claim 4, wherein at least one of the fluorescent dyes is a polyazaindacene dye of the formula:

wherein $R_1-R_6$, which may be the same or different, are hydrogen, halogen, or alkyl, alkoxy, alkenyl, cycloalkyl, arylalkyl, acyl, wherein the alkyl portions each contain fewer than about 20 carbons, or aryl, heteroaryl, alone or in combination; and $R_7$ is nitrogen, methine, or halogen-, alkyl-, alkyl-, alkoxy-, alkenyl-, cycloalkyl-, arylalkyl-, acyl-, (the alkyl portions of which each contain fewer than about 20 carbons) aryl-, or heteroaryl-substituted methine.

6. A microparticle, as claimed in claim 1, wherein at least one of the fluorescent dyes is a polyazaindacene dye of the formula:

wherein $R_1-R_6$, which may be the same or different, are hydrogen, halogen, or alkyl, alkoxy, alkenyl, cycloalkyl, arylalkyl, acyl, wherein the alkyl portions each contain fewer than about 20 carbons, or aryl, heteroaryl, alone or in combination; and $R_7$ is nitrogen, methine, or halogen-, alkyl-, alkoxy-, alkenyl-, cycloalkyl-, arylalkyl-, acyl-, (the alkyl portions of which each contain fewer than about 20 carbons) aryl-or heteroaryl-substituted methine.

7. A microparticle, as claimed in claim 6, wherein the spectral overlap allows for energy transfer that is greater than about 95%.

8. A microparticle, as claimed in claim 1, wherein the series of fluorescent dyes contains less than about 6 dyes in a total dye concentration that is between about 0.5% and 2% weight to weight.

9. A microparticle, as claimed in claim 1, wherein the ratio of initial donor to ultimate acceptor is between about 1:5 and about 10:1.

10. A microparticle, as claimed in claim 1, wherein the polymeric microparticle is polystyrene, polymethylmethacrylate, polyacrylonitrile, polyacrylamide, or polyacrolein;

the series of fluorescent dyes contains less than about 6 dyes which are different polyazaindacene dyes of the formula:

wherein $R_1$–$R_6$, which may be the same or different, are hydrogen, halogen, or alkyl, alkoxy, alkenyl, cycloalkyl, arylalkyl, acyl, (the alkyl portions of which each contain fewer than about 20 carbons) or aryl, heteroaryl, alone or in combination; and $R_7$ is nitrogen, methine, or halogen-, alkyl-, alkoxy-, alkenyl-, cycloalkyl-, arylalkyl-, acyl-, (the alkyl portions of which each contain fewer than about 20 carbons) aryl- or heteroaryl-substituted methine;

for which the total dye concentration is between about 0.8 and 1.2% (w/w); and the ratio between initial donor and ultimate acceptor dyes is between about 4:1 and about 6:1.

11. A fluorescent microparticle comprising:

a series of fluorescent dyes having an initial donor dye with a desired excitation peak and an ultimate acceptor dye with a desired emission peak, wherein the desired excitation peak and the desired emission peak are determined in a polymeric material, wherein said polymeric material is made up of polymerizable monomers, and wherein each dye in the series has a spectral overlap sufficient to allow for significant energy transfer of excitation energy to the ultimate acceptor dye, wherein said series of dyes is randomly incorporated in a polymeric microparticle comprising said polymeric material such that the total dye concentration is less than about 10% w/w and the ratio of initial donor to ultimate acceptor is between about 1:5 and about 1:10.

12. A microparticle, as claimed in claim 11, wherein the microparticle is polystyrene, brominated polystyrene, polyacrylic acid, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, or polydivinylbenzene and is less than about 15 micrometers in diameter.

13. A microparticle, as claimed in claim 12, wherein the series of dyes contains less than about 6 polyazaindacene dyes of the formula:

wherein $R_1$–$R_6$, which may be the same or different, are hydrogen, halogen, or alkyl, aldoxy, alkenyl, cycloalkyl, arylaklyl, acryl, wherein the alkyl portions each contain fewer than about 20 carbons, or aryl, heteroaryl, alone or in combination; and $R_7$ is nitrogen, methine, or halogen-, alkyl-, alkoxy-, alkenyl-, cycloalkyl-, arylalkyl-, acyl-, (the alkyl portions of which each contain fewer than about 20 carbons) aryl-or heteroarylsubstituted methine.

14. A microparticle, as claimed in claim 13, further comprising a bioreactive substance, wherein said bioreactive substance has been either bound covalently or passively adsorbed.

15. A microparticle, as claimed in claim 14, wherein said bioreactive substance is a biomolecule that is biotin, avidin, streptavidin, digoxigenin, or a nucleic acid.

* * * * *

REEXAMINATION CERTIFICATE (2863rd)

United States Patent [19]

Brinkley et al.

[11] B1 5,326,692

[45] Certificate Issued Apr. 30, 1996

[54] FLUORESCENT MICROPARTICLES WITH CONTROLLABLE ENHANCED STOKES SHIFT

[75] Inventors: John M. Brinkley, Elmira; Richard P. Haugland; Victoria L. Singer, both of Eugene, all of Oreg.

[73] Assignee: Molecular Probes, Inc., Eugene, Oreg.

Reexamination Request:
No. 90/003,738, Feb. 21, 1995

Reexamination Certificate for:
Patent No.: 5,326,692
Issued: Jul. 5, 1994
Appl. No.: 882,299
Filed: May 13, 1992

[51] Int. Cl.$^6$ .............. C12Q 1/68; G01N 33/545; C09K 11/02
[52] U.S. Cl. .............. 435/6; 435/7.92; 436/518; 436/528; 436/529; 436/531; 436/546; 436/800; 428/402; 252/301.34; 252/301.35
[58] Field of Search .................. 435/6, 7.1, 7.5, 435/7.92; 436/518, 528, 529, 530, 531, 546, 800; 427/213.34, 157; 428/402, 402.24, 407; 252/301.34, 301.35

[56] References Cited

U.S. PATENT DOCUMENTS 4,774,339  9/1988  Haugland et al. ............ 548/405

OTHER PUBLICATIONS

Pekcan, O. & Winnik, M. A., "Direct Energy–Transfer Studies on Doped and Labeled Polymer Latex Particles", *Physical Review Letters*, 61:641–644 (1988).

Fornusek, L. & Vetvicka, V., "Polymeric Microspheres as Diagnostic Tools for Cell Surface Marker Tracing", *CRC Critical Reviews in Therapeutic Drug Carrier Systems* 2(2);137–175 (1986).

*Primary Examiner*—Lora M. Green

[57] ABSTRACT

The invention relates to microparticles incorporating a series of two or more fluorescent dyes having overlapping excitation and emission spectra allowing efficient energy transfer from the excitation wavelength of the first dye in the series, transfer through the dyes in the series and re-emitted as an optical signal at the emission wavelength of last dye in the series, resulting in a desired effective Stokes shift which is controlled through selection of appropriate dyes.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 11 are determined to be patentable as amended.

Claims 2-10 and 12-15, dependent on an amended claim, are determined to be patentable.

1. A fluorescent microparticle made by the process comprising: a) selecting a series of dyes comprising an initial donor dye with a desired excitation peak and a final acceptor dye with a desired emission peak, wherein the desired excitation peak and the desired emission peak are determined in a polymeric material, and wherein said polymeric material is made up of polymerizable monomers, and wherein each dye in the series has a spectral overlap sufficient to allow for significant energy transfer of excitation energy to the final acceptor dye, b) incorporating said series of dyes in a polymeric microparticle comprising said polymeric material, wherein said series of dyes are randomly incorporated [into] *throughout* said polymeric microparticle.

11. A fluorescent microparticle comprising: a series of fluorescent dyes having an initial donor dye with a desired excitation peak and an ultimate acceptor dye with a desired emission peak, wherein the desired excitation peak and the desired emission peak are determined in a polymeric material, wherein said polymeric material is made up of polymerizable monomers, and wherein each dye in the series has a spectral overlap sufficient to allow for significant energy transfer of excitation energy to the ultimate acceptor dye, wherein said series of dyes is randomly incorporated [in] *throughout* a polymeric microparticle comprising said polymeric material such that the total dye concentration is less than about 10% w/w and the ratio of initial donor to ultimate acceptor is between about 1:5 and about 1:10.

* * * * *